United States Patent [19]

Stensaas et al.

[11] Patent Number: 4,778,467
[45] Date of Patent: Oct. 18, 1988

[54] PROSTHESES AND METHODS FOR PROMOTING NERVE REGENERATION AND FOR INHIBITING THE FORMATION OF NEUROMAS

[75] Inventors: Larry J. Stensaas; R. Joseph Todd, both of Salt Lake City, Utah; Philip M. Triolo, Enschede, Netherlands

[73] Assignee: The University of Utah, Salt Lake City, Utah

[21] Appl. No.: 884,088

[22] Filed: Jul. 10, 1986

Related U.S. Application Data

[63] Continuation-in-part of Ser. No. 603,835, Apr. 25, 1984, Pat. No. 4,662,884.

[51] Int. Cl.$^4$ .............................................. A61F 2/04
[52] U.S. Cl. .................. 623/12; 128/334 R; 128/898
[58] Field of Search .................. 623/12, 66, 1, 8; 128/334 R, 335.5, 334 C, 335; 427/2

[56] References Cited

U.S. PATENT DOCUMENTS

| | | |
|---|---|---|
| 397,861 | 2/1889 | Kelly . |
| 783,031 | 2/1905 | Fell . |
| 947,146 | 1/1910 | Von Bolton . |
| 1,151,300 | 8/1915 | Soresi . |
| 1,217,637 | 2/1917 | Rink . |
| 1,308,799 | 7/1919 | Masland . |
| 1,329,121 | 1/1920 | Hachman . |
| 1,470,707 | 10/1923 | Bates . |
| 1,983,601 | 12/1934 | Conn .................. 128/304 |
| 2,015,509 | 9/1935 | Austin .................. 148/16 |
| 2,071,250 | 2/1937 | Carothers .................. 260/106 |
| 2,127,903 | 8/1938 | Bowen .................. 128/334 |
| 2,332,826 | 10/1943 | Fryer et al. .................. 113/116 |
| 2,451,703 | 10/1948 | Weiss .................. 128/334 |
| 2,453,056 | 11/1948 | Zack .................. 128/334 |
| 2,514,665 | 7/1950 | Myller .................. 128/2 |
| 2,737,402 | 3/1956 | De Frumerie et al. .................. 285/22 |
| 2,764,683 | 9/1956 | Paust et al. .................. 250/36 |
| 3,048,177 | 8/1962 | Takaro .................. 128/334 |
| 3,155,095 | 11/1964 | Brown .................. 128/334 |
| 3,157,181 | 11/1964 | McCarty .................. 128/404 |

(List continued on next page.)

FOREIGN PATENT DOCUMENTS

81/01650 6/1981 World Int. Prop. O. .............. 623/8

OTHER PUBLICATIONS

Brooke Rutledge Seckel et al., "Nerve Regeneration through Synthetic Biodegradable Nerve Guides ...", Plastic & Reconst. Surg., vol. 74, No. 2, Aug. 1974.

(List continued on next page.)

Primary Examiner—Richard J. Apley
Assistant Examiner—Alan W. Cannon
Attorney, Agent, or Firm—Workman, Nydegger & Jensen

[57] ABSTRACT

The present invention is directed to prosthesis and methods for promoting nerve regeneration. The proximal and distal ends of a severed nerve are brought into close proximity and are enclosed by a tubular prosthesis. In one preferred embodiment, a epineurial or endoneurial monosuture is used to hold the nerve ends in close proximity. A tight seal is formed between the prosthesis and the injured nerve so as to isolate the injured nerve within the prosthesis from the rest of the body of the host. Additionally, in one preferred embodiment, nerve grafts may be incorporated into the prosthesis and nerve regeneration promoting substances may be incorporated within the nerve graft to further enhance nerve regeneration. In another preferred embodiment, a prosthesis is coated with a material which is slippery with relation to the surrounding body tissue and the prosthesis is formed of or coated with a material around the inside of the prosthesis which will substantially adhere to the severed nerve ends so as to prevent substantial movement of the severed nerve ends within the prosthesis. In yet another preferred embodiment, such an outside coating around the prosthesis terminates in two longitudinal flaps which serve to form a fluid-tight seal along the tubular prosthesis. In still another preferred embodiment, the ends of the prosthesis overlap and are formed so as to bias against each other in a spiral tube configuration, thereby providing for firm closure of the prosthesis around a variety of sizes of injured nerves. Also disclosed are various devices and methods for inhibiting the formation of neuromas, such as an open-ended tube or a neuroma-inhibition device formed as a cap member having a reservoir formed therein.

9 Claims, 4 Drawing Sheets

U.S. PATENT DOCUMENTS

| | | | |
|---|---|---|---|
| 3,221,746 | 12/1965 | Noble | 128/334 |
| 3,254,650 | 6/1966 | Collito | 128/334 |
| 3,272,204 | 9/1960 | Artandi et al. | 128/334 |
| 3,317,924 | 5/1967 | Le Veen | 3/1 |
| 3,320,947 | 5/1967 | Knoll | 128/2.1 |
| 3,357,432 | 12/1967 | Sparks | 128/334 |
| 3,387,608 | 6/1968 | Figar | 128/2.06 |
| 3,405,715 | 10/1968 | Hagfors | 128/418 |
| 3,479,670 | 11/1969 | Medell | 3/1 |
| 3,561,448 | 2/1971 | Peternel | 128/334 |
| 3,626,926 | 12/1971 | Kuzain et al. | 128/1 C |
| 3,648,295 | 3/1972 | Palma | 128/334 |
| 3,677,243 | 7/1972 | Nerz | 128/214.4 |
| 3,718,134 | 2/1973 | Brindley | 128/2.1 |
| 3,724,467 | 4/1973 | Avery et al. | 128/418 |
| 3,786,817 | 1/1974 | Palma | 128/334 |
| 3,805,793 | 4/1974 | Wright | 128/334 |
| 3,822,708 | 7/1974 | Zilber | 128/419 |
| 3,833,002 | 9/1974 | Palma | 128/334 |
| 3,841,305 | 10/1974 | Hallgren | 128/1.3 |
| 3,841,306 | 10/1974 | Hallgren | 128/1.5 |
| 3,883,901 | 5/1975 | Coquard et al. | 128/334 |
| 3,896,817 | 7/1975 | Hursen et al. | 128/419 |
| 3,915,151 | 10/1975 | Kraus | 128/1.5 |
| 3,916,905 | 11/1975 | Kuhn | 128/334 |
| 3,918,459 | 11/1975 | Horn | 128/419 |
| 3,955,560 | 5/1976 | Stein et al. | 128/2.1 |
| 3,960,151 | 6/1976 | Kuhn | 128/334 |
| 3,974,835 | 8/1976 | Hardy, Jr. | 128/334 |
| 4,019,518 | 4/1977 | Maurer et al. | 128/419 |
| 4,019,519 | 4/1977 | Geerling | 128/422 |
| 4,026,300 | 5/1977 | DeLuca et al. | 128/418 |
| 4,052,978 | 10/1977 | Eugenio | 128/2.1 Z |
| 4,056,097 | 11/1977 | Maass | 128/1.5 |
| 4,057,069 | 11/1977 | Dorffer et al. | 128/421 |
| 4,141,365 | 2/1979 | Eischell et al. | 128/404 |
| 4,157,087 | 6/1979 | Miller et al. | 128/741 |
| 4,245,638 | 1/1981 | Lebeck et al. | 128/334 |
| 4,267,842 | 5/1981 | Archibald | 128/334 |
| 4,279,256 | 7/1981 | Bucalo | 128/419 |
| 4,306,561 | 12/1981 | de Medinaceli | 128/303.13 |
| 4,331,150 | 5/1982 | Braun et al. | 128/334 |
| 4,331,157 | 5/1982 | Keller, Jr. et al. | 128/419 |
| 4,379,665 | 4/1983 | Hendershot et al. | 408/204 |
| 4,458,678 | 7/1984 | Yannas et al. | 128/155 |
| 4,534,349 | 8/1985 | Barrows | 128/334 |
| 4,669,474 | 6/1987 | Barrows | 128/334 R X |

OTHER PUBLICATIONS

Rosen et al., "Fasicular Tubilization: A Cellular Approach to Peripheral Nerve Repair", Annuals of Plastic Surg., vol. II, #5, Nov. 1983.

Uzman et al, "Mouse Sciatic Nerve Regen. through Semipermeable Tubes: A Quantitative Model", 9 Journal of Neuroscience Research, 325–338 (Apr. 1983).

F. Longo et al., "Neuronotrophic Activities Accumulate In Vivo Within Silicone Nerve Regeneration Chambers", 261, Brain Research, 109–117 (Feb. 1983).

G. Lundborg et al., "Nerve Regeneration Model and Trophic Factors In Vivo", 232, Brain Research, 157–161 (1982).

G. Lundborg et al., "Nerve Regeneration in Silicone Chambers: Influence of Gap Length and of Distal Stump Conponents", 76, Experimental Neurology, 361–375 (1982).

G. Lundborg et al., "In Vivo Regeneration of Cut Nerves Encased in Silicone Tubes", 41, Journal of Neuropathology and Experimental Neurology, 412–422, No. 4 (1982).

H. Molander et al., "Regeneration of Peripheral Nerve Through a Polyglactin Tube", 5, Muscle and Nerve, 54–57 (1982).

J. Rosen et al., "Suture and Sutureless Methods of Repairing Experimental Nerve Injuries", Chapter 25 of Nerve Repair and Regeneration; Its Clinical and Experimental Basis (D. L. Jewett and H. R. McCarroll, eds.) (1979).

Sir Sydney Sunderland, "Nerves and Nerve Injuries", Chapters 1, 2, 46, 48, and 49 (pp. 3–60, 533–550, and 569–602), 2d Ed., published by Churchill Livingstone (1978).

Alan Peters et al., "The Fine Structure of the Nervous System: The Neurons and Supporting Cells", Chapters 6 and 12 (pp. 181–230 and 323–331), 2d Ed., published by the W. B. Saunders Co. (1976).

"Silastic Nerve Cuff", advertising bulletin of Dow Corning Corporation, Midland, Mich., Bulletin 51-046A (Jan. 1974).

T. Ducker et al., "Peripheral Nerve Injuries: A Comparative Study of the Anatomical and Functional Results Following Primary Nerve Repair in Chimpanzees", 133, Milit. Med., 298–302 (1968).

P. Weiss, "Sutureless Reunion of Severed Nerves with Elastic Cuffs of Tantulum", 1, J. Neurosurg., 219–225 (1944).

"Nerve Tube Implant" (source and date unknown).

W. Kuhn et al., "A Nerve Implant Prosthesis for Facilitating Peripheral Nerve Regeneration", (unknown whether this reference has ever been published).

Alix Freedman, "Nerve Regeneration Seen in Procedure Using Protein Tube", Wall Street Journal, p. 23 (Nov. 5, 1986, Western Edition).

PROSTHESES AND METHODS FOR PROMOTING NERVE REGENERATION AND FOR INHIBITING THE FORMATION OF NEUROMAS

RELATED APPLICATIONS

This application is a continuation-in-part of copending application Ser. No. 603,835 now U.S. Pat. No. 4,662,884 filed Apr. 25, 1984, for "PROSTHESES AND METHODS FOR PROMOTING NERVE REGENERATION."

BACKGROUND

2. The Field of the Invention

The present invention relates to nerve prostheses and the repair of injured nerves. In particular, the present invention is directed to prostheses and methods for promoting nerve regeneration and for inhibiting the formation of neuromas in traumatized nerves.

2. The Prior Art

Nerves are vital to the basic operation and function of the human body. Injury to a nerve can result in a partial or total loss of the sensation, control, or use of a member or portion of the body. Although methods currently exist for surgically repairing nerve tissue, such methods are not always possible and are commonly not completely successful in achieving a restoration of sensation, control, and use of the affected portion of the body.

One method of repair involves the use of very fine sutures (multiple microsutures) to sew the severed nerve ends together. Such microsurgical procedures are typically conducted with the use of a microscope, and are extremely tedious and time consuming. Additionally, such microsurgical procedures are often not successful, particularly in view of the large amount of time which typically transpires before surgery can be completed, as well as in view of the amount of manipulation which is required while the ends of the injured nerve are being sewn together using these microsurgical techniques.

Where substantial nerve injury has occurred, it is often physically impossible to suture the severed nerve ends together. Thus, for more major nerve injuries, nerve grafts are often used as a nerve replacement. However, these nerve grafts suffer from many drawbacks. First, the chances for success in achieving nerve regeneration using such grafts has been extremely unpredictable. Second, there is the potential for an autoimmune response by the body to the nerve graft or any other material that is not isogenic to the patient.

Not only has the prior art failed to provide reliable prostheses and methods for regenerating nerve tissue, but the prostheses and methods used by the prior art often result in an extremely undesirable and painful condition referred to in the art as a "neuroma." Simply stated, a neuroma consists of a mass of nerve fibers growing irregularly from the injured proximal nerve end and without connection to the distal nerve end. This condition can be so painful, that it has driven some patients to suicide. Unfortunately, there are no consistently effective methods known in the prior art for inhibiting the formation of neuromas.

It would, therefore, be a significant advancement in the art to provide effective prostheses and methods for promoting regeneration of nerve tissue. It would also be an advancement in the art to provide such prostheses which could be implanted in a patient without tedious and time-consuming installation techniques.

It would be still a further advancement in the art if the prostheses could incorporate a nerve graft which is not rejected by the body. It would be yet another significant advancement in the art to provide a method for inhibiting and substantially preventing the formation of neuromas. Such prostheses and methods are disclosed and claimed herein.

BRIEF SUMMARY AND OBJECTS OF THE INVENTION

The present invention provides nerve prostheses and methods for promoting nerve regeneration in a variety of different situations. In each situation, a tubular prosthesis which is made of biocompatible material and which is impermeable to fluids associated with the injured nerve is used to promote regeneration of the injured nerve.

A first application of the present invention is where there is no gap (or a very short gap) between the injured nerve ends. Using epineurial monosutures, the proximal and distal ends of the severed nerve are brought together and held into close proximity to each other, preferably touching, but at least within about 0.5 millimeters. Next, the proximal end of the severed nerve and the distal end of the severed nerve are enclosed within the tubular prosthesis. The prosthesis is firmly secured to the nerve, particularly, around the proximal end of the nerve by the resilient properties of the tubular prosthesis, so as to seal the severed nerve ends from the environment outside of the prosthesis.

Thus, the tubular prostheses and methods of the present invention serve (1) to maintain the proximal and distal nerve ends in close proximity without using the prior art procedure of suturing the very ends of the nerve together, (2) to isolate the nerve ends from the environment outside of the prosthesis, and (3) to prevent escape and unregulated growth of nerve fibers outside of the nerve itself.

A second application of the present invention is where more substantial injury to the nerve has occurred, i.e., where there is a gap of about 2 centimeters or more between the severed nerve ends after the nerve ends have been coapted using a monosuture. In this situation, it may be preferable to use an animal nerve graft in conjunction with the tubular prosthesis of the present invention. According to the present invention, a nerve graft is prepared so as to minimize the potential for rejection of the nerve graft by the body, and the nerve graft is positioned within the tubular prosthesis. The proximal and distal ends of the severed nerve are enclosed within the tubular prosthesis as discussed above.

In this second application of the present invention, however, the proximal end of the severed nerve is positioned in close proximity to one end of the nerve graft within the tubular prosthesis, i.e., within at least about 0.5 millimeters, while the distal end of the severed nerve is similarly positioned and held within close proximity to the other end of the nerve graft within the prosthesis.

In some instances, it may be desirable to impregnate the animal nerve graft with nerve regeneration promoting substances or components to further promote regeneration of the injured nerve. Nerve regeneration promoting substances such as fibronectin, laminin angiogenesis factors, nerve growth factor, extracts of central nervous tissue, and Schwann cells may be used for this purpose.

It is, therefore, an object of the present invention to provide effective prostheses and methods for promoting nerve regeneration in a variety of different types of nerve injury.

Another object of the present invention is to provide nerve prostheses which are quickly and easily implanted into a patient.

A further object of the present invention is to provide nerve prostheses which may incorporate a nerve graft that has been treated in order to minimize the potential for rejection of the graft by the body.

A still further object of the present invention is to provide apparatus and methods for inhibiting and substantially preventing the formation of neuromas in injured nerve tissue.

These and other objects and features of the present invention will become more fully apparent from the following description and appended claims, taken in conjunction with the accompanying drawings.

DETAILED DESCRIPTION OF THE PREFERRED EMBODIMENTS

A. General Discussion of Nerve Structure and the Principles of Nerve Regeneration The following general discussion relating to nerve structure and the regeneration of a nerve is given so that the particular problems which have been solved by the present invention may be better understood. It should be noted that while some of the following discussion is based upon facts and principles which are known in the art, much of the following discussion is based upon particular discoveries made by the inventors which have not heretofore been known and understood, and which are important in solving the problems which are addressed by the present invention.

Moreover, it will be understood that a few portions of the following discussion are based upon theory which has been formulated to explain the phenomenon of nerve regeneration. This information is given so as to fully enable one of ordinary skill in the art to understand the operation of and the importance of the novel features of the present invention in promoting the regeneration of nerve tissue and in inhibiting or substantially preventing the formation of neuromas. Nevertheless, it will be appreciated that while such theory aids in understanding the present invention, the effectiveness and utility of the present invention does not necessarily depend upon the absolute accuracy of such scientific theory.

The structure of a typical nerve is quite complex. Within a single nerve is a plurality of "fasciculi" or "funiculi" interconnected by connective tissue known as the epineurium. The epineurium consists mainly of dense collagen, blood vessels, and fibroblasts.

Each funiculus within the nerve actually contains a multitude of nerve fibers or "axons"; hence, a funiculus is often referred to as a "nerve bundle." Typically, each funiculus comprises the following elements: (1) a perineurium, (2) nerve fibers or axons, (3) Schwann cells (with or without a myelin sheath), (4) blood vessels, (5) fibroblasts, and (6) endoneurial fluid.

The perineurium is a layer of cells around each nerve bundle or funiculus. The tissue within the perineurium surrounding the individual nerve fibers of a funiculus is what is referred to as the endoneurium. Endoneurial fluid occupies the endoneurium within funiculi.

The perineurium acts as an impermeable barrier to keep foreign substances out of the funiculus and to keep endoneurial fluid contained within the funiculus. Thus, the perineurium serves to retain a fluid environment which is favorable to the axons and Schwann cells within the funiculus. The myelin sheath, which is found around many axons and which acts as an insulator for the axons, is made by the Schwann cells which are positioned around the axon. The elongated lamina or endoneurial tube. The Schwann cells also serve to form a protoplasmic sheath for unmyelinated nerve fibers.

Inside of the perineurium of each funiculus are found trophic substances which stimulate, inter alia, (1) the growth of blood vessels, (2) the fibroblasts to make collagen, (3) the growth of the axons, and (4) the maintenance of the nerve cell bodies. These trophic substances are produced by the Schwann cells and are found only in the endoneurial compartment of each funiculus; these trophic substances are not outside of the funiculus in the epineurial region of the nerve.

Nerve impulses pass down the membrane of each axon by utilizing discontinuities in the Schwann cells and in the myelin sheath of myelinated axons; these discontinuities are known as "nodes of Ranvier." The nerve impulse progresses from one node of Ranvier to the next node of Ranvier down the axon, and the presence of myelin serves to speed up its propagation.

When a nerve is injured, the Schwann cells attack the damaged and degenerating nerve tissue so as to degrade the nerve tissue into components which can be removed through the blood capillaries. During this time, the Schwann cells begin to divide and accelerate their production of the trophic substances which: (1) stimulate the growth of the regenerating nerve fibers or axon sprouts arising from the individual nerve fibers, (2) stimulate the proliferation of fibroblasts which are capable of producing collagen, (3) stimulate the blood vessels to grow, and (4) stimulate the regeneration of the injured perineurium. As can be seen, the Schwann cells play an important role in the regeneration of the nerve tissue which has been subjected to severe trauma or injury.

Upon injury to a nerve, many events transpire other than activation and proliferation of the Schwann cells. For example, each myelinated axon of the severed nerve divides into a multiplicity of fine regenerating nerve fibers or axon sprouts, which sprouts are frequently enclosed within a small perineurial sheath. The group of regenerating nerve sprouts enclosed within the new perineurial sheath and the Schwann cells associated with each regenerating nerve sprout of the axon, are collectively referred to as a "regenerating unit." In the regeneration of a nerve, the regenerating units only grow out from the proximal end of the severed nerve; this growth is directed towards the distal end of the severed nerve.

These regenerating units continue to grow and extend across the gap between the proximal and distal ends of the severed nerve. Regenerating sprouts which continue down the distal end of the severed nerve are eventually guided by Schwann cells to muscle or sensory sites.

Bridging of the gap by the regenerating units is necessary in order for there to be successful regeneration of the nerve. After the gap is bridged by the regenerating units, the individual perineurial sheaths around the nerve fibers of the myelinated axon of each regenerating unit disappear, and a single perineurial sheath forms around the regenerated funiculus.

When the nerve is first severed, cytoplasm oozes from the transected axons of the severed nerve, and the transected axons die back to a node of Ranvier. Subsequently, the regenerating units begin to develop; these regenerating units grow and extend out of the proximal end of the severed nerve towards the distal end thereof.

In order for a regenerating unit to bridge the gap, it is essential that there be a sufficient quantity of Schwann cells present in the area of the gap. When the axons of the regenerating units finally meet Schwann cells in the distal end of the severed nerve, the production of Schwann cells, perineurial cells, and collagen ceases, but the axons continue to grow along the channels formed by the elongated Schwann cells and the endoneurial tubes.

If regenerating units do not reach the distal end of the severed nerve, a neuroma may result. A neuroma is the collective result of the misdirected growth of many regenerating units. In a neuroma, growth of the regenerating units generally occurs in a random fashion in directions substantially away from the distal end of the severed nerve. In fact, frequently, the regeneration units of a neuroma will grow within the epineurium of the proximal nerve end in a direction substantially opposite of the distal nerve end.

One reason that neuromas form in the area of injured nerve tissue is that Schwann cells of the growing regenerating units, which begin to extend from the proximal end of the severed nerve, emit trophic or growth stimulating substances which are necessary for nerve regeneration. These substances escape from the open, growing ends of the regenerating units, diffusing in all directions, thus encouraging unregulated development of fibroblasts and capillaries in many different directions and leading to growth of the regenerating units in many different directions. In this regard, the endoneurial fluid flowing out of the nerve acts as a carrier for the trophic substances and causes them to be emitted from the ends of the regenerating units.

Since the fibroblasts surrounding the regenerating units synthesize collagen in the presence of trophic substances, a neuroma is typically characterized by the progressive formation of a dense collagen matrix. As the dense collagen builds up, it eventually binds the regenerating units, and may cause pain upon mechanical deformation or stimulation of the regenerated axons.

Thus, it will be appreciated that one of the important principles of the present invention in promoting regeneration of nerve tissue is that the regenerating units are preferably directed in a straight path toward the distal end of the severed nerve. As will be discussed in more detail hereinafter, one of the key features of the prostheses within the scope of the present invention is that they both orient and "pave the road" for the regenerating units by promoting oriented growth of the fibroblasts and the capillaries. This enables the regenerating units to more easily find the distal end of the severed nerve, thereby minimizing the possibility that a neuroma will be formed. Moreover, as discussed hereinafter, the present invention also provides for directing the trophic substances in a path between the proximal and distal ends of the severed nerve, and for avoiding the escape of these trophic substances to other areas surrounding the severed nerve.

B. Presently Preferred Embodiments of the Present Invention

Reference is now made to the drawings wherein like parts are designated with like numerals throughout. Refering now to FIG. 1, a tubular nerve prosthesis made in accordance with the present invention is generally designated 10. Nerve prosthesis 10 preferably has a generally constant inner diameter; the nerve prosthesis may also be configured with rounded or tapered ends 12 and 14 which are formed by gradually decreasing the thickness of the wall of tubular prosthesis 10 at its respective ends. It has been found that by employing rounded or tapered ends in a prosthesis made in accordance with the present invention, the outer surface of the prosthesis is allowed to move with respect to other nearby structures, thus reducing or minimizing trauma to surrounding tissues as well as reducing or minimizing tension on the nerve during normal movement.

Figure 1:
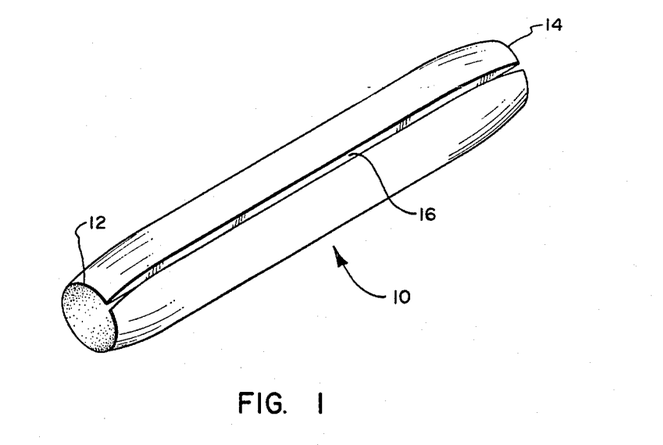
FIG. 1 is a perspective view of one embodiment of a tubular prosthesis within the scope of the present invention.

Importantly, nerve prosthesis 10 is made of a layer of a resilient, yet renitent, biocompatible material which is impermeable to fluids associated with nerve tissue. Such resiliency and renitency may be provided, for example, by using a layer of a flexible biocompatible material. Additionally, it has been found presently preferable to construct the nerve prosthesis from a material which is transparent so as to enable a surgeon employing the prostheses to see the position of the injured nerve within the prosthesis when used in accordance with the present invention.

For example, materials such as silicone rubber, polyurethane, Teflon (Teflon is a trademark of the DuPont Corporation), and nitrocellulose have been found to be suitable for these purposes of the present invention. Silicone rubber is presently the most preferred material for the prostheses of the present invention formed in accordance with FIGS. 1 and 2, since it is elastic and has been found not to adhere to the surrounding connective tissue. As will be readily appreciated, it is desirable to minimize the adherence of the prosthesis to the surrounding connective tissue. However, it will be understood that the foregoing materials are given by way of example only, and that other materials may be suitable for forming nerve prostheses in accordance with the present invention.

For purposes of the present invention, it is very important that nerve prosthesis 10 be fabricated of a material which is substantially impermeable to fluids associated with nerve tissue. In particular, it is important that prosthesis 10 be constructed of a material which will not allow escape of substantial amounts of the trophic substances and fluids from the interior of the prosthesis to the exterior of the prosthesis. Such impermeability keeps the trophic substances within the tubular prosthesis so as to encourage nerve regeneration in a direct path from the proximal end to the distal end of the severed nerve.

It is also important that the wall of prosthesis 10 be of sufficient resiliency and renitency so that it will close around the injured nerve ends and form a close, fluid-tight seal around the injured nerve. It has been found that by constructing the wall with a thickness of about 10%–40% of the inner diameter of prosthesis 10, sufficient resiliency and renitency are obtained for this purpose where prosthesis 10 is made of silicone rubber. This percentage range may of course decrease somewhat with more strongly elastic materials. Table I, which follows, provides examples of prostheses within the scope of the present invention, correlating maximum exemplary values for the diameter and tubular wall thickness of various prostheses made of silicone rubber:

TABLE I

| Wall Thickness of Prosthesis (mm) | Inner Diameter of Prosthesis (mm) |
| --- | --- |
| 0.35 | 1.0 |
| 0.35 | 1.5 |
| 0.41 | 2.0 |
| 0.46 | 2.5 |
| 0.51 | 3.0 |
| 0.56 | 4.0 |
| 0.61 | 5.0 |

Although the wall of each prosthesis made in accordance with the present invention should be of sufficient thickness to supply the resiliency and renitency needed to allow the prosthesis to close around the injured nerve ends and form a close, internal pressure-resistant seal, at the same time, it is desirable to minimize the size of the prosthesis so that it can be easily accommodated within the tissue of the host. Hence, it is presently preferable to construct the prosthesis with a wall having sufficient thickness to provide for the resiliency needed in order to form a close seal, yet thin enough that the prosthesis can be easily accommodated within the host.

It will be appreciated that the minimum wall thickness which will be necessary in order to provide the required resiliency and renitency will vary from material to material. By selecting a material which is resilient and renitent in relatively small thicknesses, a prosthesis may be provided which both provides the required resiliency and renitency, yet optimizes the accommodation of the prosthesis within the host.

The exemplary wall thicknesses set forth hereinabove, i.e., about 10%–40% of the inner diameter of the prosthesis, is the range of wall thicknesses which have been found to produce these results when the prosthesis is made of silicone rubber. Similarly, the exemplary wall thicknesses given in Table I above are also for silicone rubber. it will be appreciated that other materials may be more resilient and renitent than silicone rubber at smaller thicknesses, and that thus, the thickness ranges and examples set forth hereinabove with respect to silicone rubber are given by way of example only and should not be considered restrictive. Indeed, by using materials such as polyurethane to form a prosthesis in accordance with the present invention, wall thicknesses significantly smaller than those characteristic of silicone rubber may be used to provide the resiliency and renitency needed to form a close seal in accordance with the present invention.

Tubular nerve prosthesis 10 is also preferably provided with a longitudinal slit 16 which extends along the entire length of the tubular prosthesis. Slit 16 allows for the longitudinal opening of prosthesis 10 so as to permit insertion of the ends of the severed nerve into the prosthesis.

Importantly, prosthesis 10 is made of a resilient, yet renitent, material and has an inner diameter corresponding roughly to the outer diameter of the injured nerve.

The resilient nature of prosthesis 10 helps the prosthesis to close to form a close seal around the severed nerve when the severed nerve ends are inserted into the prosthesis and the pressure applied to open the prosthesis at slit 16 is released. Because of the renitent nature of the prosthesis and because a tissue capsule typically forms around the prosthesis within about 2-3 days, the prosthesis will resist internal pressures, thereby serving to prevent such internal pressures from causing the prosthesis to reopen along slit 16.

Hence, it will be appreciated that although a gap is shown along slit 16 in FIG. 1 for purposes of illustration, the walls of prosthesis 10 close to form a relatively tight seal along slit 16. Thus, in the closed position, nerve prosthesis 10 functions as though it has a continuous tubular surface with no slit.

Prosthesis 10 is thus self-closing in that the wall of resilient, yet renitent, material restores itself and favors the formation of an encapsulation such that fluids associated with the nerve will not generally be capable of escaping from prosthesis 10. In this manner, a close, fluid-tight seal is provided along slit 16 so that prosthesis 10 acts as a continuous device. Hence, it will be appreciated that slit 16 serves to accommodate insertion of a severed nerve funiculus into the prosthesis 10, and is subsequently sealed off after insertion by the action of the walls of the prosthesis and by formation of the encapsulation so as to maintain the close seal which is of importance in the present invention.

The closely fitting prosthesis of the present invention provides a straight path for the regenerating units extending out of the proximal end of the severed nerve, so that they may more easily find the distal end of the severed nerve. Hence, the closely fitting prosthesis minimizes the chances of the regenerating axons being misrouted, thereby minimizing the chances of the formation of a neuroma.

Additionally, the closely fitting and impermeable prosthesis of the present invention maintains the trophic substances within a tubular pathway so as to encourage axon growth within the prosthesis, while substantially discouraging axon growth in any other direction. Hence, the tubular prostheses of the present invention provide for proper orientation of the regenerating units, and channels the trophic substances necessary for nerve regeneration in the proper direction.

Although there may be many different methods for fabricating a prosthesis in accordance with the present invention, one presently preferred example of a procedure for manufacturing a nerve prosthesis within the scope of the present invention is given in Example 1 below.

EXAMPLE 1

A presently preferred method for making a nerve prosthesis within the scope of the present invention involves the injection of liquid silicone rubber into a mold configured so as to form a prosthesis substantially similar to that illustrated in FIG. 1.

It has been found desirable to configure the mold so that the outer surface of the prosthesis is smooth, while the inner surface of the prosthesis is somewhat rough or textured. The smooth outer surface allows the prosthesis to slip with respect to the adjacent connective tissue, and the rough inner surface of the prosthesis provides for better adherence of the prosthesis to the nerve ends after the prosthesis is positioned. The prosthesis is then slit longitudinally to provide a prosthesis substantially similar in configuration to the prosthesis shown in FIG. 1.

Figure 3A:
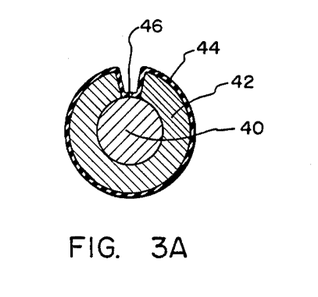
FIG. 3A is a transverse cross-sectional view of a tubular prosthesis within the scope of the present invention wherein the method of manufacture is illustrated as using a mandrel.

Another procedure which may be used in manufacturing prostheses within the scope of the present invention results in a prosthesis having even a better seal along the slit of the prosthesis. Such a procedure and prosthesis can best be understood by reference to FIGS. 3A and 3B. Referring more particularly to FIG. 3A, a mandrel 40 is inserted into a tubular prosthesis 42 formed, for example, in accordance with the procedure of Example 1. Mandrel 40 is of slightly larger diameter than the inner diameter of prosthesis 42, thereby forcing the slit of the prosthesis open so as to form a longitudinal gap. The prosthesis 42 and mandrel 40 are then dipped in a solution of silicone rubber in a solvent such as freon (chlorotrifluoroethane) or toluene to form, for example, a 10% solution. The solvent is allowed to evaporate under vacuum, thereby forming a thin coating 44 of silicone rubber around prosthesis 42.

Figure 3B:
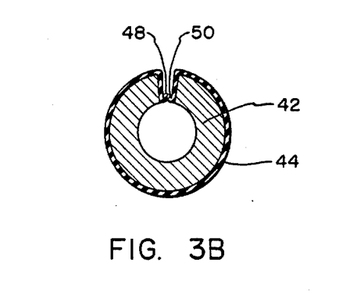
FIG. 3B is a transverse cross-sectional view of the embodiment of the tubular prosthesis of FIG. 3A after the tubular prosthesis has been formed and removed from the mandrel.

Upon drying, the thin coating of silicone rubber 44 is slit longitudinally at site 46 along the longitudinal gap to form two longitudinal flaps 48 and 50 which are best illustrated in FIG. 3B. Upon removing mandrel 40 from prosthesis 42 as shown in FIG. 3B, flaps 48 and 50 are forced together in close apposition so as to form a tight seal along the longitudinal slit of the prosthesis 42.

The thin coating of silicone rubber 44 and flaps 48 and 50 formed by such a coating help to provide a close, fluid-tight seal along the longitudinal slit of the prosthesis and may find particular utility where the diameter of the severed nerve to be repaired is slightly greater than the inner diameter of prosthesis 42.

When a prosthesis is made in accordance with the embodiment of FIGS. 3A and 3B, it has been found presently preferable to construct prosthesis 42 of polyurethane and coating 44 of silicone rubber. Polyurethane is more resilient than silicone rubber in thin layers. On the other hand, silicone rubber does not substantially adhere to the nerve tissue, but is quickly encapsulated.

By constructing the inner portion of the prosthesis of polyurethane, the prosthesis may be constructed of a thinner layer of material than would be needed using the silicone rubber, and yet still provide the necessary resliency and renitency needed.

It will be appreciated that a variety of combinations of materials may be used to construct prostheses in accordance with the embodiments of FIGS. 3A and 3B. This, of course, would be done by selecting a desired material for main prosthesis structure 42, and another desired material for coating 44. On the other hand, it will also be appreciated that, if desired, main prosthesis structure 42 and coating 44 may be constructed of the same material. Materials which may be used for either main prosthesis structure 42 or coating 44 include, for example, silicone rubber, polyurethane, Teflon, and nitrocellulose.

In choosing the appropriate materials for prosthesis structure 42 and coating 44, however, it should be kept in mind that it is desirable to select materials which will substantially prevent adhesion between the body tissue and the exterior of the prosthesis, as such adhesion may prevent the prosthesis from moving freely and thereby result in the sensation of pain. However, it is desirable to choose materials which will promote rapid development of a capsule between the nerve tissue and the interior of the prosthesis as it may further promote regeneration of the nerve tissue by holding the coapted nerve ends in close proximity to each other. As will be appreciated, it is therefore usually most referable to construct prosthesis structure 42 and coating 44 from two different materials which have these respective properties.

Figure 2:
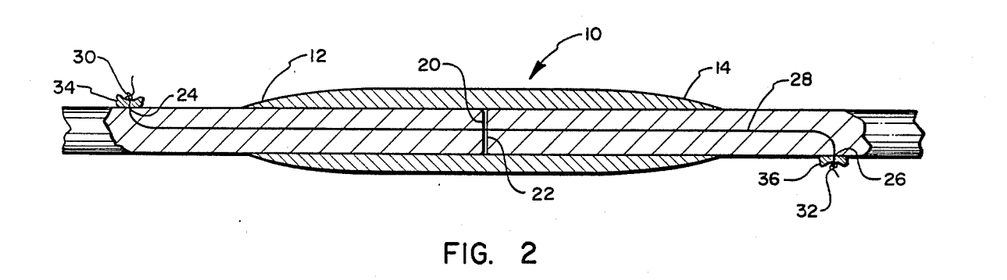
FIG. 2 is a longitudinal cut-away, cross-sectional view of the embodiment of the tubular prosthesis of FIG. 1 as used to treat a nerve injury where there is only a very small gap (or no gap) between the injured nerve ends.

Referring now to FIG. 2, the application of the nerve prosthesis of the present invention to a first type of nerve injury is illustrated. One of the most common types of nerve injury involves the situation where the nerve has been severed so that there is only a very small gap (or no gap) between the ends of severed nerve. In this situation, the tubular nerve prosthesis 10 is used to bring the proximal end 20 and the distal end 22 of the severed nerve into close proximity in the following manner.

Figure 9:
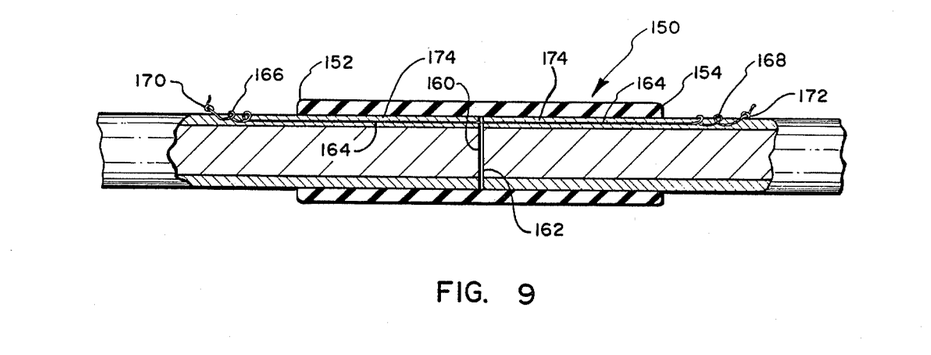
FIG. 9 is a longitudinal cut-away, cross-sectional view of a tubular prosthesis within the scope of the present invention which employs a epineurial monosuture.
Figure 10:
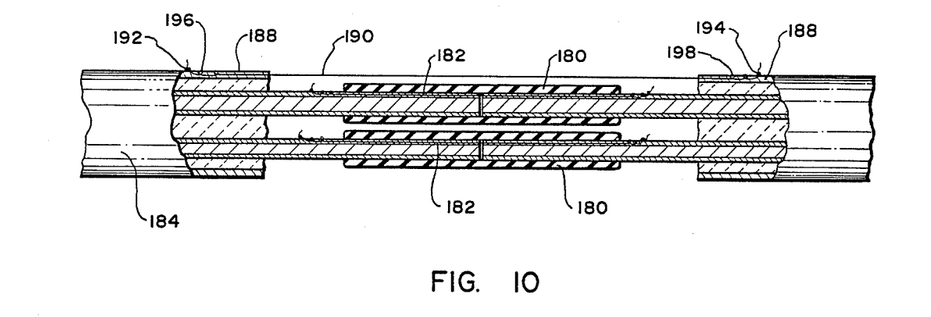
FIG. 10 is a longitudinal cut-away, cross-sectional view of the application of an epineurial monosuture and several tubular prostheses in accordance with the present invention to reunite the individual nerve fasicles of a severed whole nerve.
Figure 11:
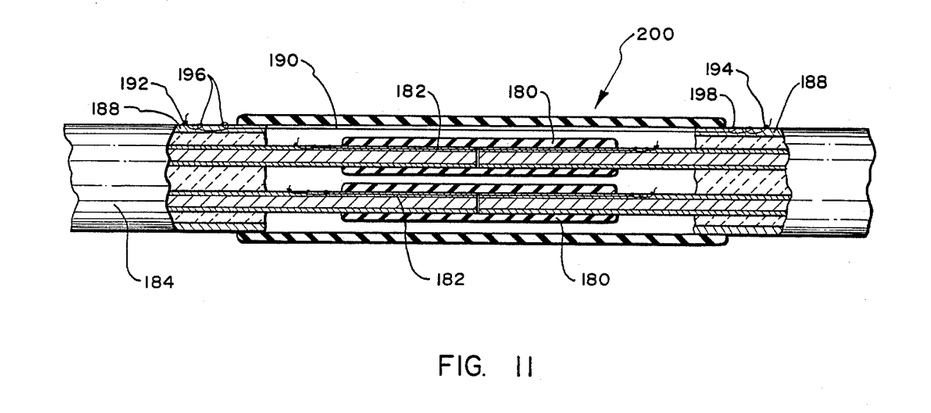
FIG. 11 is a longitudinal cut-away, cross-sectional view of the embodiment of FIG. 10, further showing the use of a prosthesis within the scope of the present invention to surround the individual repaired nerve fasicles and to reunite the severed ends of the whole nerve.

Preferably, a fascicular monostructure is first used to coapt severed nerve ends 20 and 22 before the nerve prosthesis is placed around the severed nerve ends. For this purpose, either a perineurial or an endoneurial monosuture may be employed. The epineurial monosuture, which is presently preferred, is illustrated in FIGS. 9-11 and will be explained in more detail hereinafter. The endoneurial monosuture is illustrated as monosuture 28 in the embodiment of FIG. 2.

The endoneurial monosuture 28 is formed by introducing a long needle carrying a very fine suture thread through site 26 of the perineurium of the injured nerve (typically, about 6-7 millimeters from the distal end), drawing the needle and thread through the interior of distal nerve end 22 into the interior of proximal nerve end 20, and withdrawing the needle and thread at site 24 of the perineurium of the injured nerve (typically, about 6-7 millimeters from the proximal end).

Once the endoneurial monosuture 28 is in place, tension can be applied to the ends of the monosuture so as to bring nerve ends 20 and 22 into close proximity, preferably within about 0.5 millimeters of each other or even so that the nerve ends are in contact with each other. The suture ends are then tied at sites 24 and 26 to form knots 30 and 32, respectively. Additionally, a piece of connective tissue 34 and 36 may be used at each suture knot to act as a pad and distribute tension between the knot and the perineurium of the nerve. Hence, endoneurial monosuture 28 serves to coapt the proximal and distal nerve ends 20 and 22 so that there is an extremely small gap and relatively no tension between the two nerve ends 20 and 22.

Although it is presently preferable to use a monosuture in connection with prosthesis 10, it will be appreciated that the prosthesis of the present invention may be used without such a monosuture or that other techniques for bringing the nerve ends into close proximity may be used. The reason that it has been found preferable to use a monosuture with the prosthesis of the present invention is that the monosuture places the nerve ends in close proximity while the prosthesis is placed into position; moreover, the monosuture continues to serve to help maintain the nerve ends in such close proximity after the prosthesis has been placed into position.

Although the tubular nerve prosthesis may be constructed of any desirable length, for this and many other applications of the present invention, it is generally desirable to construct the nerve prosthesis of sufficient length that the prosthesis will extend at least about 3-4 millimeters over the proximal end 20 and at least about 3 millimeters over the distal end 22 of the severed nerve.

The slit 16 in the tubular prosthesis facilitates its insertion around nerve ends 20 and 22. The resilient walls of the prosthesis retract to form a close seal and to effectively retain fluids within the prosthesis.

In this regard, it should be noted that for purposes of the present invention, the most important area for forming such a close seal is around proximal end 20 of the severed nerve. This is because it is from proximal end 20 that the regenerating units begin to grow. Thus, by securing tubular prosthesis 10 closely around the nerve ends 20 and 22, and particularly around proximal end 20, the regenerating units are directed directly towards distal end 22 and the trophic substances emanating from proximal end 20 and distal end 22 are prevented from spreading into areas outside of the injured nerve. This serves not only to promote regeneration of the injured nerve, but also to inhibit the formation of a neuroma by controlling the growth and direction of the regenerating units and trophic substances.

As shown in FIG. 2, the monosuture may be used to coapt and secure the injured nerve ends in close proximity. However, when the monosuture is used, it is preferable to apply the terminal knots of the monosuture far away from severed nerve ends 20 and 22 so as to minimize the undesirable effects which would occur, for example, if the very nerve ends themselves were sutured together. As will be appreciated, there are means other than the monosuture which may be used to maintain nerve ends 20 and 22 in close proximity. One such means will be discussed in more detail hereinafter with respect to FIG. 4.

An optional procedure which may be used in connection with the placement of a nerve prosthesis within the scope of the present invention involves a small, localized crush of the proximal nerve end before positioning it within the tubular prosthesis. By applying a small localized crush to the proximal nerve end at a point located about 1-2 centimeters from the point of severance, most of the axoplasmic oozing from the proximal nerve end is stopped. It has been found desirable to stop the oozing of the axoplasm from the proximal nerve end so that the nerve ends can be cleanly coapted without interference by the axoplasm. Following such a crush to the proximal nerve end, no edema and axoplasm is present in the gap at the time the regenerating axons reach the gap between the nerve ends. Since edema and axoplasm tend to cause the regenerating axons to be misrouted, minimizing the presence of edema and axoplasm in the gap is desirable.

Such a crushing procedure also serves to delay the arrival of the regenerating axons out of the proximal end of the severed nerve. Hence, since the gap is relatively free and clear of edema and axoplasm by the time the regenerating axons reach the gap between the proximal and distal nerve ends, there is a smaller chance that the regenerating axons will be misrouted and that a neuroma will result.

Although this crushing procedure results in the develoment of fewer regenerating sprouts, the axons which are produced are typically larger and do not tend to divide into smaller axons as much as those axons which have not first been crushed. Hence, with fewer and more rapidly regenerating axons, the larger axons have a better chance of bridging the gap between the severed nerve ends and in achieving successful regeneration of the nerve.

It is further believed that the crushing procedure allows the proliferating Schwann cells to migrate out into the gap between the severed nerve ends before the regenerating axons reach this gap. Thus, the gap may be bridged with Schwann cells before the transected axons reach the gap.

If some of the axons start regenerating immediately, as is the case when the proximal nerve end is not crushed, upon reaching the gap, they grow in a random fashion (in the absence of Schwann cells) and may escape into the epineurium. Conversely, when the Schwann cells have a chance to spread into the gap between the severed nerve ends before the arrival of the regenerating units, they encourage the axon growth in a path towards the distal end of the nerve and also reduce the chances of a neuroma.

It will be appreciated that the optional procedure discussed hereinabove for crushing the severed proximal nerve end at a point located about 1-2 cm from the point of severance, applies not only to the placement of a nerve prosthesis in accordance with the embodiment of FIG. 2, but also to the placement of nerve prosthesis in accordance with the embodiments of FIG. 3, FIG. 4, FIG. 5, and FIG. 6 discussed herein, as well as other embodiments of the present invention.

Figure 4:
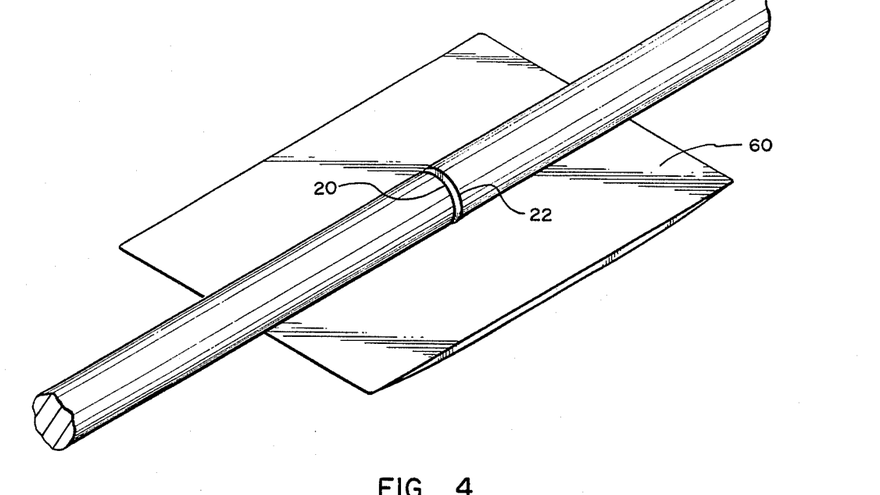
FIG. 4 is a perspective view of another preferred embodiment of a tubular prosthesis within the scope of the present invention as used to treat a nerve injury where there is only a very small gap (or no gap) between the injured nerve ends.

Referring now to FIG. 4, an illustration of a second preferred embodiment of the present invention is shown as it is used to treat a nerve injury where there is only a very small gap (or no gap) between the injured nerve ends. As will be appreciated, this second preferred embodiment may or may not use a monosuture to bring the severed nerve ends together within the prosthesis.

In this second preferred embodiment of FIG. 4, proximal end 20 and distal end 22 are first painted or coated with a fast drying biocompatible polymer, such as nitrocellulose, dissolved in a quickly evaporating solvent such as an ether/alcohol mixture (for example, 50% by volume ethyl ether mixed with 50% by volume ethyl alcohol). Ends 20 and 22 are then positioned in close proximity to each other, preferably within at least about 0.5 millimeters, as with the embodiment of FIG. 2. However, in this second preferred embodiment, the prosthesis is formed from a flat sheet of material 60. Nitrocellulose has been found to work well as a material for flat sheet 60 in this second preferred embodiment; nitrocellulose is commercially available and is sold, for example, under the trade name Parlodian.

Nitrocellulose sheet 60 is drawn around the nerve ends 20 and 22 and the edges of the nitrocellulose material 60 are solvent welded together, for example, with ether, so as to form a tubular prosthesis around the severed nerve ends. When sheet 60 is so formed, the resultant prosthesis has the same general tubular configuration as prosthesis 10 in FIGS. 1 and 2, but need not be as thick as prosthesis 10 of FIGS. 1 and 2 and may or may not have rounded ends. Moreover, there will be a ridge in the prosthesis formed from sheet 60 where the edges of the sheet are solvent welded together.

In the embodiment of FIG. 4, it is generally desirable to paint nerve ends 20 and 22 with nitrocellulose so that a tight seal will be formed between the nerve ends 20 and 22 and the tubular prosthesis formed from sheet 60. Since nitrocellulose adheres well to the collagen in the epinurium of the severed nerve, nitrocellulose is the presently preferred material for the prosthesis of FIG. 4. Additionally, as nitrocellulose dries, it shrinks; thus an even closer seal with the severed nerve is formed with the nitrocellulose prosthesis of FIG. 4. However, it will be appreciated that other materials may also adhere well to the epineurium of the severed nerve and may also be used in accordance with the present invention.

From the foregoing, it will be appreciated that sheet 60 which forms the prosthesis in the embodiment of FIG. 4 need not be constructed of resilient or renitent material as is the case with the embodiment of FIG. 2, since this prosthesis does not rely upon the wall properties of resiliency and renitency to form a close seal around the injured nerve ends. Rather, in the embodiment of FIG. 4, the close seal is formed by wrapping sheet 60 around the nerve ends 20 and 22 to form a close seal in accordance with the present invention, and further, by adherence of the painted nerve ends 20 and 22 to sheet 60. Hence, it will be appreciated that the prosthesis of FIG. 4 need not be constructed of material as thick as the material forming the prosthesis embodiment of FIG. 2.

Figure 5:
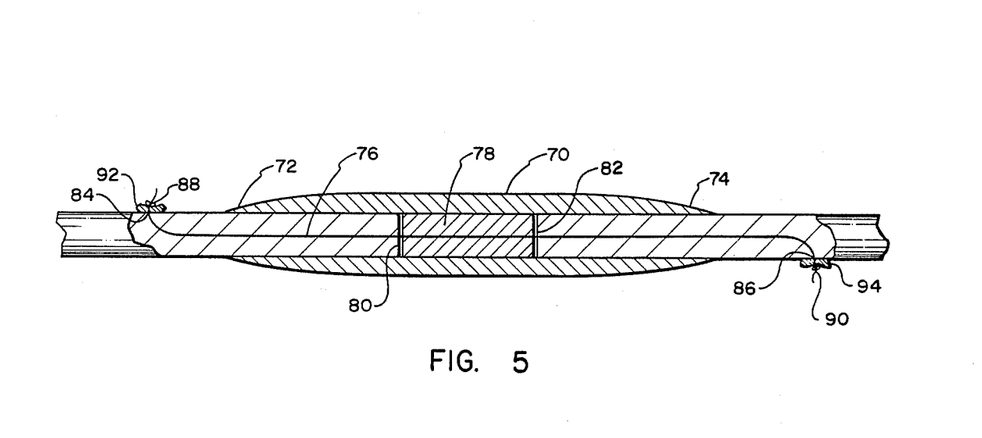
FIG. 5 is a longitudinal cut-away, cross-sectional view of a tubular prosthesis within the scope of the present invention as used to treat a nerve injury where there is a gap of about two centimeters or more between the severed nerve ends.

Referring now to FIG. 5, the application of the present invention to a second type of nerve injury is illustrated. In this second type of injury, more substantial injury to the nerve has occurred such that there is a one to two centimeter (or larger) gap between the severed nerve ends. Because of the larger gap, the tubular prosthesis used, designated 70 in FIG. 5, is, of course, somewhat longer than the tubular prosthesis used to bridge short gaps.

As illustrated in FIG. 5, tubular prosthesis 70 has rounded ends 72 and 74 similar to the ends of prosthesis 10 of FIGS. 1 and 2. Additionally, a monosuture such as endoneurial monosuture 76 may also be used with this embodiment. Thus, the primary difference between tubular prosthesis 70 used in FIG. 5 and prosthesis 10 used in FIG. 2, besides the obvious difference in length, is that an animal nerve graft 78 is incorporated into prosthesis 70. Thus, as illustrated in FIG. 5, the tubular prosthesis acts as a perineurial homologue, while the animal nerve graft acts as an endoneurial homologue.

The purpose of the animal nerve graft 78 is to provide a scaffold for the regenerating units as they grow from proximal end 80 towards distal end 82 of the severed nerve. This nerve graft may be derived from any suitable source, such as bovine or rabbit sources.

An important feature of the present invention is to remove histocompatibility factors from the animal nerve graft so as to minimize the potential of rejection of the nerve graft by the body of the host, and yet retain the important structural features of the animal nerve graft to provide a scaffold for the regenerating nerve.

A procedure for preparing the nerve graft according to the presently preferred procedure of the present invention is as follows. First, the animal nerve graft is placed in fresh deionized water every two hours for a period of about eight to twelve hours. The absence of osmotic substances in deionized water serves to swell and rupture cells in the nerve graft, and diffusion to remove the cytoplasm bound by these cells as well as the proteins in the cell membranes of the nerve graft which include histocompatibility factors.

After treatment by the deionized water, the following structural features of the animal nerve graft preferably and desirably remain intact: (1) the basal lamina of the endoneurial tubes, (2) the lipid components of cell membranes, and (3) the collagen of the epineurium and endoneurium. It is important that the basal lamina be left intact since it is the basal lamina which attracts Schwann cells, and as discussed above, Schwann cells are essential to proper nerve regeneration.

After treatment with the deionized water, the nerve graft is lyophilized (freeze-dried) to maintain its shape. Additionally, by drying the nerve graft in this manner, the graft has a tendency to attract the trophic substances from the proximal and distal ends of the severed nerve when used within a tubular prosthesis in accordance with the present invention.

After treatment with the deionized water, the lyophilized nerve graft may be immersed into an aqueous solution of nerve regeneration promoting substances, such as nerve growth factor. (Nerve growth factor may be obtained, for example, from male mouse saliva, by procedures well-known in the art.) The nerve graft is then again dried by lyophilization.

Subsequently, the nerve graft is preferably sterilized by any well-known technique, such as gamma radiation. Finally, the ends of the nerve graft are cut so as to provide even ends, and the nerve graft is ready for incorporation into the nerve prosthesis 70.

To achieve implantation in this second type of nerve injury, the injured nerve ends are secured within the prosthesis much in the same way as when there is a very small gap between the severed nerve ends. Prosthesis 70 is opened along its longitudinal slit, and nerve graft 78, as well as nerve ends 80 and 82, are place within the interior of prosthesis 70 as shown in FIG. 5, such that nerve ends 80 and 82 are in close proximity to the ends of nerve graft 78. Preferably, proximal end 80 is brought to within at least about 0.5 millimeters from one end of nerve graft 78, while distal end 82 is preferably brought to within at least about 0.5 millimeters from the other end of nerve graft 78 within prosthesis 70.

A monosuture such as endoneurial monosuture 76 may be used to secure nerve ends 80 and 82 in such close proximity with the ends of nerve graft 78. Monosuture 76 is formed much in the same way as monosuture 28 of the embodiment of FIG. 2, however, a longer needle is needed in order to situate monosuture 76. Thus, the needle and monosuture 76 are inserted through the perineurium at site 86 of the injured nerve and are introduced through the endoneurium of distal end 82, thence through animal nerve graft 78, into proximal nerve end 80, and finally through site 84 of the perineurium of the injured nerve. Monosuture 76 is tied to form knots 88 and 90 at sites 84 and 86, respectively, and optionally, a pad of connective tissue 92 and 94, respectively, may be used to cushion each knot against the surface of the injured nerve.

Prosthesis 70 is then closely secured around the injured nerve in substantially the same fashion as with the embodiment illustrated in FIG. 2, i.e., by allowing the thick-walled, resilient, yet renitent, prosthesis 70 to return to its closed position. However, as with the embodiment of the present invention illustrated in FIG. 2, nerve prosthesis 70 of FIG. 5 may be secured to the injured nerve by other means.

Moreover, prosthesis 70 of FIG. 5 may be secured to the injured nerve by forming the prosthesis in a fashion similarly to the embodiment set forth in FIG. 4. This is done by forming the tubular prosthesis from a sheet of material, for example, nitrocellulose, and wrapping the nitrocellulose sheet around both the nerve graft 78 and the nerve ends 80 and 82 to form the tubular prothesis. The edges of the prosthesis may then be solvent sealed with ether, as explained previously with respect to the embodiment of FIG. 4. As with the embodiment of FIG. 4, nerve ends 80 and 82 should be painted with nitrocellulose so as to achieve proper adherence of nerve ends 80 and 82 to the nitrocellulose sheet which forms the tubular prosthesis.

Figure 6:
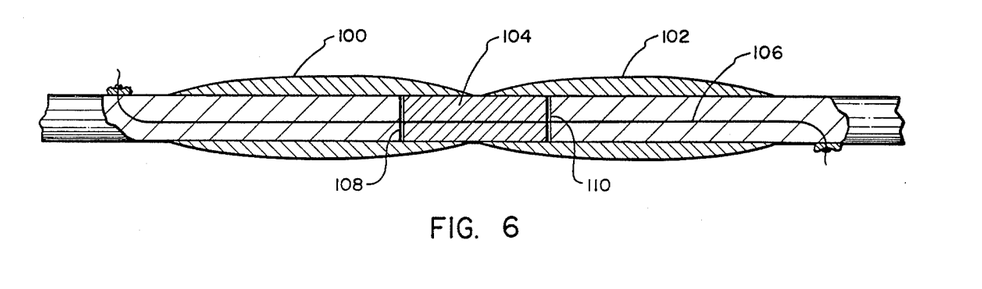
FIG. 6 is a longitudinal cut-away, cross-sectional view of a plurality of tubular prostheses within the scope of the present invention as used to treat a nerve injury where there is a gap of about two centimeters or more between the severed nerve ends.

Referring now to FIG. 6, a second embodiment of the application of the present invention to the second type of nerve injury is illustrated. The primary difference between the second embodiment of FIG. 6 and the first embodiment of FIG. 5 is that in the embodiment of FIG. 6, two prostheses are used instead of one. When a nerve graft is used in connection with the present invention, the embodiment of FIG. 6 is presently preferred over the embodiment of FIG. 5 in many instances, since better revascularization is often experienced when using the embodiment of FIG. 6.

In this second embodiment of FIG. 6, two tubular prostheses 100 and 102, similar in construction to prosthesis 10 of FIG. 1, are employed in conjunction with an animal nerve graft 104. Alternatively, prostheses 100 and 102 could be constructed according to the embodiment of FIG. 4.

Animal nerve graft 104 is prepared in identical fashion to animal nerve graft 78 of FIG. 5. Each end of nerve graft 104 is then enclosed within either tubular prosthesis 100 or 102 as illustrated in FIG. 6, and the injured nerve ends 108 and 110 are enclosed within the prostheses in the same fashion as the first embodiment of FIG. 5.

Proximal end 108 of the severed nerve is situated in prosthesis 100 so as to be in close proximity with one end of animal nerve graft 104, while distal end 110 of the severed nerve is situated in prosthesis 102 such that distal end 110 is in close proximity with the other end of the animal nerve graft. A monosuture such as endoneurial monosuture 106 is used to bring and hold nerve ends 108 and 110 into close proximity with the ends of nerve graft 104, much in the same manner as with the embodiment of FIG. 5. Protheses 100 and 102 are then secured to injured nerve ends 108 and 110 and nerve graft 104 by proper closure of prostheses 100 and 102.

In treating a nerve injury where there is a large gap, it may be desirable to impregnate the animal nerve graft with one or more nerve regeneration promoting substances to further encourage regeneration of the nerve tissue across the gap.

Some nerve regeneration promoting substances which have been found to be useful for purposes of the present invention include fibronectin, angiogenesis factors, nerve growth factor, extracts of mature and immature central nervous tissue, e.g., central nervous system homogenate, and Schwann cells and the products of Schwann cell cultures. These nerve regeneration promoting substances are introduced directly into the animal nerve graft which is to be situated inside of the tubular nerve prosthesis.

Figure 7A:
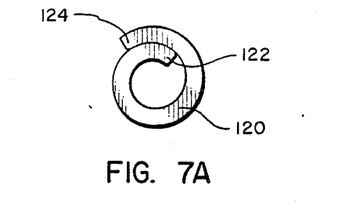
FIG. 7A is a transverse cross-sectional view of a spiralled tubular prosthesis within the scope of the present invention formed so that the edges of the prosthesis overlap.
Figure 7B:
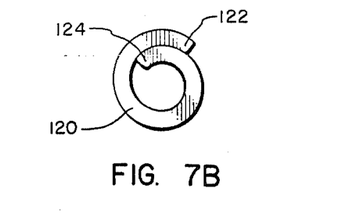
FIG. 7B is a transverse cross-sectional view of the embodiment of the spiralled tubular prosthesis of FIG. 7A with the overlapping edges of the prosthesis reversed so as to form a firm seal therealong.

Another preferred embodiment of the present invention relates to a spiralled nerve prosthesis 120 which is best illustrated in FIGS. 7A and 7B. Using one presently preferred method of manufacture, prosthesis 120 is formed by injecting a liquid, such as silicone rubber or any other suitable material, into a mold having the configuration shown in FIG. 7A. The resultant prosthesis 120 has an inner longitudinal edge 122 and an outer longitudinal edge 124 which overlap. After forming the prosthesis into the configuration shown in FIG. 7A, longitudinal edges 122 and 124 of the prosthesis are reversed such that edge 122 becomes the outer edge and edge 124 becomes the inner edge.

Upon reversal of edges 122 and 124, outside prosthesis edge 122 will tend to return to its original position shown in FIG. 7A, and thus prosthesis edge 122 shown in FIG. 7B will exert an elastic force inwardly toward inside prosthesis edge 124. Similarly, inside prosthesis edge 124 shown in FIG. 7B will have a tendency to return to its original position (shown in FIG. 7A), and thus will exert an elastic force outwardly against prosthesis edge 122. The resulting configuration of the prosthesis 120 shown in FIG. 7B is an overlapping or spiralled configuration which tends to seal itself along its longitudinal edges.

One advantage of the spiralled tube embodiment of the present invention shown in FIG. 7B is that the prosthesis is expandable to accommodate nerves and funiculi of various sizes, thus eliminating the need for many prostheses of different sizes for treating different sized nerves and funiculi. In this regard, prosthesis edges 122 and 124 serve to form a close, fluid-tight seal in accordance with the present invention around various size nerves, and thus provide a snugly fitting prosthesis which is adjustable to a range of nerve or funiculi diameters.

Besides the liquid injection molding technique described above with respect to FIGS. 7A and 7B, another preferred method for manufacturing a spiralled tube prosthesis in accordance with the embodiment of FIG. 7B involves the use of a material having a significant amount of residual stress. In using this technique, a tube is formed from a material having a significant amount of residual stress, such as polyurethane or other suitable material.

After the tube is formed, a longitudinal slit is formed down the length of the tube, in a similar fashion to the embodiment of FIG. 1. However, because of the residual stress of the material used in this embodiment, the longitudinal edges along the slit tend to curl in on themselves to assume the configuration shown in FIG. 7B. Hence, it will be appreciated that by carefully selecting an appropriate material having the requisite residual stress, a spiralled tube prosthesis in accordance with the embodiment of FIG. 7B may be formed simply by splitting an extruded tube formed of such material.

It will also be appreciated that, when using the spiralled tube configuration in forming a tubular nerve prosthesis in accordance with the present invention, it is important that the resultant spiralled tube provide a close seal along the overlapping edges of the tube so as to achieve the benefits of the present invention set forth herein. Such a close seal can be provided by the techniques outlined herein, such as the liquid injection molding technique and reversal of the resultant prosthesis edges, as well as the technique of forming a tubular prosthesis of a material having an adequate degree of residual stress such that the edges of the tube will fold in upon themselves once the tube is slit.

However, it will be appreciated that there may be other methods for forming a spiralled tube prosthesis in accordance with the present invention so as to provide closure along the overlapping edges, and the scope of the present invention is not restricted to these two exemplary methods for forming a spiralled tube prosthesis. For example, it may be possible to form a spiralled tube prosthesis by curing a sheet of material so that it curls, and then reversing the inside and outside edges of the cured prosthesis for better closure.

In experiments conducted using nerve prostheses formed substantially in accordance with the embodiment of FIG. 1, it has been observed that, upon implantation of such a prosthesis in experimental animals, an impermeable sealant or encapsulation occurs around the inner and outer surfaces of the tubular prosthesis. This relatively impermeable sealant or encapsulation covers substantially the entire surface area of the prosthesis, both the inner prosthesis surface enclosing the injured nerve ends and the outer prosthesis surface adjacent the body tissue surrounding the prosthesis. This encapsulation is formed by the host and is believed to further promote regeneration of the injured nerve tissue.

In this regard, it has been observed that such an encapsulation develops relatively quickly, typically in less than a week from implantation of the prosthesis. Thus, the encapsulation provides a provisional seal which structurally improves over time. This encapsulation is believed to be formed of thin layers of fibroblasts with collagen deposited between the layers of fibroblasts so as to form a tough, closely adherent enclosure. In this arrangement, the encapsulation serves to provide a better seal between the injured nerve ends and the surrounding environment, and also serves to strengthen the repair site.

Moreover, formation of the encapsulation around the inner and outer surfaces of the prosthesis further serves to prevent endoneurial fluid from escaping out of the prosthesis. Thus, unregulated growth of the regenerating axons out of the prosthesis wall through, for example, the longitudinal slit formed along the prosthesis of the embodiment of FIG. 1 is further inhibited.

The tubular nerve prostheses of the present invention may be used to promote regeneration of whole nerves, groups of funiculi, or individual funiculi, as desired. If the nerve is small, it may be desirable to use the prosthesis to unite the entire nerve. If the nerve is large, it may be desirable to use several prostheses to unite individual funiculi or groups of small funiculi.

The tubular nerve prostheses of the present invention provide a means for bringing the proximal and distal nerve ends together without actually suturing the nerve ends together using multiple microsutures. Thus, the present invention avoids the problems of the prior art wherein the regenerating axons are misrouted by suturing the very nerve ends together so as to place tension on the nerve ends and complicate the gap area between the nerve ends, thereby increasing the chances of neuroma formation. Moreover, the tubular nerve prostheses of the present invention serve to guide the regenerating units toward the distal end of the nerve within a closely fitting tube so as to promote regeneration of the nerve tissue and at the same time prevent growth of the regenerating axons in other directions so as to prevent the formation of a neuroma.

Additionally, the impermeable nature of the tubular nerve prostheses of the present invention serves to keep trophic substances within the prosthesis so as to further promote nerve regeneration and inhibit misdirected growth of the regenerating axons. The impermeability of the prosthesis also serves to isolate the animal nerve graft, when incorporated into the prosthesis, from the rest of the body of the host. This substantialy minimizes the chance of an immune response by the body resulting in rejection of the nerve graft.

The closely fitting nature of the tubular nerve prostheses of the present invention also serves to maintain the trophic substances within the prosthesis and to isolate the nerve regeneration process from the rest of the body of the host. Finally, the tubular nerve prosthesis and monosuture provide structural support for keeping the nerve ends positioned closely together or in close proximity with the animal nerve graft, while avoiding the disadvantages of the prior art technique of suturing the nerve ends directly together using multiple microsutures.

As mentioned herein, the prostheses of the present invention which may be used to promote nerve regeneration may also be used to inhibit the formation of neuromas. For example, a prosthesis formed in accordance with the embodiment of FIG. 1 may be used to inhibit the formation of a neuroma. Additionally, a prosthesis formed in accordance with the embodiment of FIG. 1 without the longitudinal slit could also be used.

In applying the tubular enclosures of the present invention so as to inhibit the formation of neuromas, only the proximal end of the severed nerve is enclosed within the tubular enclosure. Thus, for example, when applying the tubular enclosure 10 of FIG. 1 to a nerve so as to inhibit neuroma formation, the proximal end of the severed nerve is inserted within end 12 of the tubular enclosure so as to form a close seal therearound, in similar fashion as with the nerve regeneration application. Preferably, the other end 14 of tubular enclosure 10 remains open, and the distal end of the severed nerve is not placed within the tubular enclosure.

The close fit of the tubular enclosure 10 when used as a neuroma inhibition device and the impermeability of the tubular enclosure serve to make this an effective neuroma inhibition device. Tubular enclosures (about 1-2 centimeters in length) formed substantially in accordance with the embodiment of FIG. 1 but without a longitudinal slit have been used as neuroma inhibition devices in rat experiments. The regenerating nerve fibers which extended from the proximal ends of the rat nerves in these experiments generally continued down the tubular enclosures for a short distance and then tapered off without forming a terminal enlargement (neuroma) or extensive outgrowth (nerve regenerate).

The effectiveness of the tubular enclosures in inhibiting neuroma formation observed in these experiments is thought to be attributed to several factors. For example, the absence of any substrate within each tubular enclosure for encouraging growth of the growing nerve fibers tends to inhibit their growth.

Second, it has been observed that when using the neuroma inhibition devices of the present invention, a fine textured matrix tends to form in the immediate proximity of the proximal nerve end. This fine textured matrix has been preliminarily identified by electron microscopy as a proteinaceous material. It is believed that this proteinaceous material contains inhibitory substances which not only inhibit the growth of the regenerating axons, but also discourage the development of other cells which normally accompany the nerve regenerate.

Figure 8A:
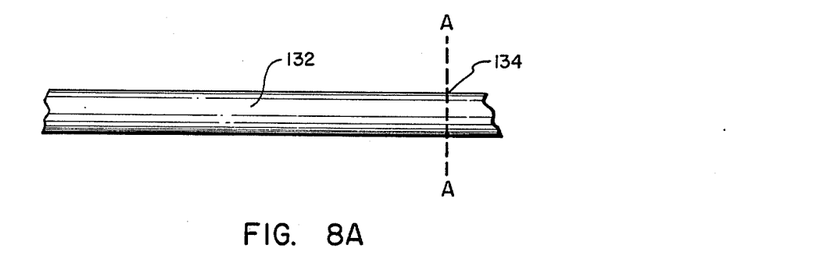
FIG. 8A illustrates the first step in one presently preferred method for manufacturing and applying a neuroma inhibition device in accordance with the present invention, which neuroma inhibition device includes a nerve cap having a reservoir formed therein. In this first step shown in FIG. 8A, the proximal end of the severed nerve is trimmed, if necessary, and the nerve end is further prepared for placement of the neuroma inhibition device therearound.
Figure 8B:
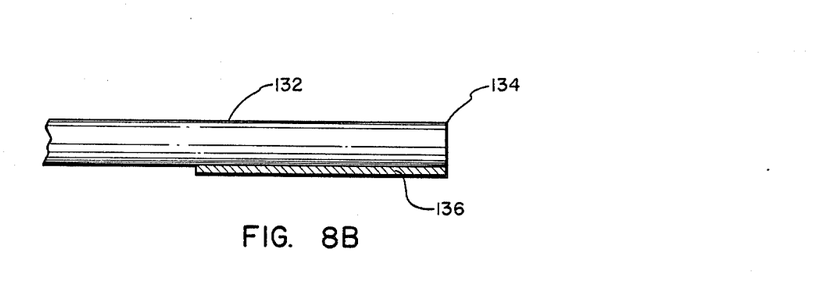
FIG. 8B illustrates the second step of the presently preferred method for manufacturing and applying a neuroma inhibition device of FIG. 8A wherein a trough shaped base member is attached to the proximal nerve end.
Figure 8C:
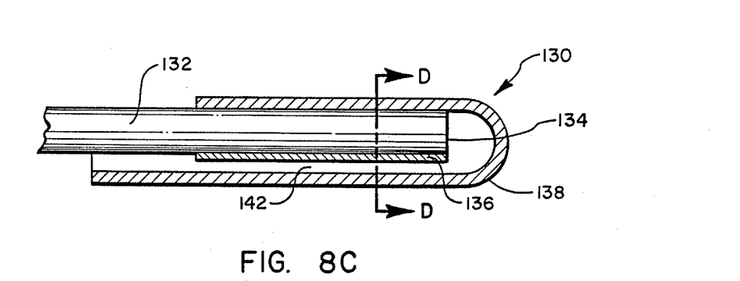
FIG. 8C illustrates the third step of the presently preferred method for manufacturing and applying a neuroma inhibition device of FIGS. 8A–8B wherein a nerve cap member is placed around the proximal nerve end and is secured thereto.
Figure 8D:
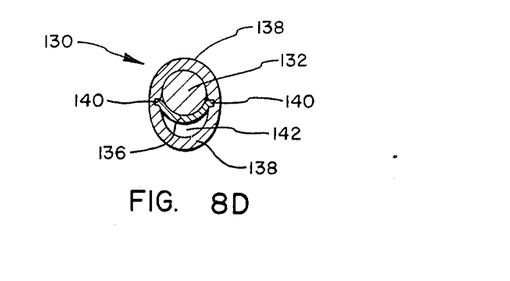
FIG. 8D is a cross-sectional view of the neuroma inhibition device illustrated in FIG. 8C taken along D—D of FIG. 8C.

Another neuroma inhibition device within the scope of the present invention involves the use of a nerve cap having a reservoir formed therein, and one presently preferred embodiment of such a nerve cap is generally designated 130 in FIG. 8C and 8D. Neuroma inhibition cap 130 is designed to fit over the proximal end of the severed nerve so as to inhibit the formation of a neuroma therefrom. One presently preferred method of preparation of the neuroma inhibition cap 130 is illustrated in FIGS. 8A-8D.

Referring first to FIG. 8A, the proximal end of a severed nerve 132 is prepared by trimming off the rough end of the nerve along line A—A shown in FIG. 8A so as to provide a relatively even edge 134 at the very end of proximal nerve end 132 and so as to expose the endoneurium of the severed nerve. Next, the sterility of the nerve end 132 is preferably assured by the limited topical application of of absolute alcohol or other antiseptic agent. Severed nerve end 132 is then coated with an adhesive substance such as cellulose nitrate.

Referring now to FIG. 8B, a trough shaped base member 136 made of such material as silicone rubber or other suitable material is then applied to the bottom peripheral side of nerve end 132 as shown in FIG. 8B. If necessary, it is preferable to again trim proximal nerve end 132 so that edge 134 is even and substantially flush with base member 136 as shown in FIG. 8B.

Referring now to FIG. 8C, a tubular nerve cap member or endoneurial fluid reservoir 138, made of a material which is substantially impermeable to fluids associated with the severed nerve, is then affixed to the adhesive around the upper peripheral side of nerve end 132 by sliding cap member 138 onto nerve end 132 so as to assume the position shown in FIG. 8C. Nerve cap member 138 preferably has a bottom peripheral side which extends beyond the top peripheral side so as to form a larger reservoir 142 which is discussed in more detail below.

As shown more specifically in FIG. 8D, in one presently preferred embodiment of the present invention, trough shaped base member 136 is configured with two flanges 140 which engage corresponding slots formed within cap member 138 so as to provide for secure attachment between cap member 138 and base member 136.

As seen in FIGS. 8C and 8D, the placement of nerve cap member 138 around nerve end 132 so as to engage base member 136 provides for the formation of a reservoir 142 between the nerve cap 138 and base member 136. Reservoir 142 serves to collect the fluids leaking out of proximal nerve end 132, thus providing a collection chamber for those fluids.

Surprisingly, although the trophic substances which leak out of the end of a severed proximal nerve end tend to stimulate growth of cells outside of the nerve as set forth hereinabove in greater detail, these fluids also are believed to contain inhibitory substances which build up inside the tube to inhibit growth of the regenerating axons. Such a belief is based upon observations of inhibited growth when these fluids are contained within the tubular enclosure. Thus, by maintaining these fluids within the tubular enclosure or reservoir 142, growth of the regenerating axons is inhibited, thus minimizing the potential for the formation of a neuroma. Reservoir 142 thus serves to retain the inhibitory substances in close proximity to the regenerating nerve fibers so as to provide a continuing deterrent to the resumption of regeneration and the development of a neuroma.

Another benefit of the neuroma inhibition device 130 of the present invention is that nerve cap 138 provides a protective, non-compressible covering for severed proximal nerve end 132, thus protecting the severed proximal nerve end from the application of pressure. As will be appreciated, application of pressure to severed proximal nerve end 132 would trigger undesirable nerve impulses and result in pain. Thus, the non-compressible space provided by neuroma inhibition device 130 minimizes the potential for such pain.

Further, neuroma inhibition device 130 is designed to stay in place indefinitely, thus eliminating the possibility of neuroma formation which might otherwise occur if the device were to slip off the severed nerve end. Although not experimentally verified, it is also believed that the inhibitory substances within reservoir 142 of the present invention may serve to deter the proliferation of Schwann cells, thus further discouraging growth of the regenerating axons.

It will be appreciated that the neuroma inhibition devices of the present invention may be used around individual fascicles or funiculi, or around groups of fascicles or funiculi as desired.

As explained previously, it is often preferable to use a perineurial or endoneurial monosuture in conjunction with the nerve prostheses of the present invention. In this regard, the perineurial monosuture is presently preferred over the endoneurial monosuture. Thus, the endoneurial monosutures illustrated at 28, 76, and 106 in the embodiments of FIG. 2, 5, and 6, respectively, as well as in all other embodiments of the present invention where a monosuture may be used, may also be formed and are preferably formed as perineurial monosutures. Such a perineurial monosuture is illustrated in the embodiment of FIG. 9.

FIG. 9 represents the application of a nerve prosthesis in accordance with the present invention to the first type of nerve injury similar to the embodiment of FIG. 2. Thus, in the embodiment of FIG. 9, a tubular nerve prosthesis generally designated 150 is used to bring the proximal end 160 and the distal end 162 of the severed nerve into close proximity in the following manner.

First, surrounding tissue such as endoneurial and epineurial tissue is removed from the proximal end 20 and the distal end 22 just far enough to allow for placement of prosthesis 150. The proper radial alignment of the proximal end 160 and the distal end 162 is then identified by noting the location of blood vessels, axons, etc. Once aligned, the proximal end 160 and the distal end 162 are coapted using the fascicular epineurial monosuture 164.

The fascicular epineurial monosuture 164 is formed by introducing a long needle carrying a very fine suture thread into the fascicular epineurium of one end of the injured nerve, e.g., about 5 millimeters from the lesion site along the proximal end 160. A knot 170 is tied at this position of about 5 millimeters from the lesion site, and one or more loops 166 may be formed through the perineurium in order to distribute tension at the point of suture termination. Such a looping procedure is optional and may be used as needed in order to so distribute the tension as required by the particular situation.

The needle and thread are then drawn axially through the interior of the perineurium 174 of the proximal end 160 and into the fascicular epineurium of the distal end 162. The needle and thread are continually drawn through the fascicular epineurium of the distal end 162 and are then brought to exit the fascicular epineurium 174 at a position of about 5 centimeters from the lesion site along distal end 162, so as to position the monosuture within the perineurium 174 of the severed nerve ends 160 and 162 as shown in FIG. 9. Again, if desired, one or more anchor loops 168 may be used to secure the fascicular epineurial monosuture on the distal end 162.

The proximal and distal nerve ends 160 and 162 are then drawn into apposition by pulling gently on the needle and thread, and a suture knot 172 is tied to complete the monosuture. Subsequently, prosthesis 150 (having a slit formed therein) is placed around the coapted nerve ends 160 and 162 in the same way as with the embodiment of FIG. 2.

It will be understood that the foregoing procedure for placing fascicular epineurial monosuture 164 into position may be reversed that is, the fascicular epineurial monosuture 164 may be started in the distal end 162 and finished in the proximal end 160 if desired. Further, instead of a single fascicular epineurial monosuture 174, it would be possible to form two perineurial monosutures to serve the function of perineurial monosuture 174, with each perineurial monosuture having one knotted end at the lesion site (not shown) of the injured nerve with the other end or knot tied at about 5 millimeters from either the proximal or distal nerve end. Moreover, it will be appreciated that, where desired or needed, it would be possible to employ a plurality of fascicular epineurial monosutures 174 in order to secure and coapt the nerve ends 160 and 162.

Although ends 152 and 154 of prosthesis 150 are shown in FIG. 9 as being relatively square and not rounded as the ends 12 and 14 of prosthesis 10 illustrated in FIG. 2, ends 152 and 154 are merely set forth to show that other configurations of the prosthesis are possible. Thus, it will be understood that the rounded end configuration is still presently preferred.

When it is desired to reunite an injured whole nerve having a plurality of fascicles, a plurality of prostheses and fascicular epineurial monosutures may be used to reunite the individual fascicles of the injured nerve, as shown in the embodiment of FIG. 10. In the embodiment of FIG. 10, two such nerve fascicles are shown united by tubular nerve prostheses 180 which correspond to prosthesis 150 in FIG. 9, and perineurial monosutures 182 which correspond to perineurial monosuture 164 in FIG. 9. Thus, as shown in FIG. 10, as many prostheses as desired may be used to reunite individual nerve fascicles of a whole nerve which has been severed.

When reuniting a whole nerve which has been severed, whether or not the individual fascicles are also individually reunited and repaired using prostheses in accordance with the present invention, it is presently preferable to reunite the severed whole nerve ends using a large superficial epineurial monosuture as also illustrated in FIG. 10. Referring to FIG. 10, severed whole nerve proximal end 184 and severed whole nerve distal end 186 may be more closely brought together using a superficial epineurial monosuture 190 in accordance with the following procedure.

First, the whole nerve ends 184 and 186 are separated from the surrounding tissue. Preferably, at least one tension distribution monosuture is placed in the epineurium, such as epineurial monosuture 190, in the following fashion.

The superficial epineurial monosuture 190 is formed by introducing a long needle carrying a very fine suture thread through the epineurium 188 of one of the severed whole nerve ends, such as proximal nerve end 184. A knot 192 is tied, and the suture is looped through the epineurium 188 a few times to form suture loops 196 and thereby distribute the tension at the point of suture termination. The suture is then drawn axially through the superficial epineurium 188 and exits the epineurium at the stripped area between the nerve ends 184 and 186. The suture is continued along this area until it reaches the epineurium 188 of opposing distal nerve end 186, and the suture is drawn axially through this superficial epineurium 188 to an exit point along nerve end 186. As with the other nerve end, a series of anchor loops 198 are preferably formed, and the whole nerve ends 184 and 186 are drawn into closer apposition by placing tension on the suture. A knot 194 is then tied so as to complete the epineurial monosuture.

The knots 192 and 194 are preferably formed about 5-10 millimeters from their respective nerve ends 184 and 186. As with the fascicular epineurial monosuture, it will be appreciated that the superficial epineurial monosuture 190 may also be formed in just the reverse fashion, i.e., by starting at the distal nerve end 186 and proceeding towards the proximal nerve end 184.

Once one superficial epineurial monosuture 190 is in place, the tension of the individual fascicles within the whole nerve is significantly reduced, thereby greatly facilitating repair of the individual nerve fascicles. Hence, the individual fascicles may then be reunited using prostheses 180 and fascicular epineurial monosutures 182 in accordance with the procedure set forth for the embodiment of FIG. 9. Once each of the individual fascicles sought to be repaired have been reunited, additional epineurial monosutures similar to epineurial monosuture 190 may be placed in the epineurium of the whole nerve so as to provide greater stability to the repair site and so as to prevent subsequent damage thereto. In this regard, it has presently been found preferable to employ from about two to about four superficial epineurial monosutures when uniting a whole nerve. However, it will be appreciated that more or fewer epineurial monosutures may be used in this regard, and that the precise number of epineurial monosutures employed will necessarily depend upon the size and nature of injury of the whole nerve involved.

It will be understood that the epineurial monosuture 190 of the embodiment of FIG. 10 may be used with or without the prostheses 180 and perineurial monosutures 182 to reunite severed whole nerve ends. Further, if desired, the entire repair site of the whole nerve may be wrapped with a relatively large tubular prosthesis so as to totally insulate the neural environment around the repair site. Such a wrapping prosthesis is shown in FIG. 11.

Referring now to FIG. 11, a relatively large tubular prosthesis formed in accordance with the present invention is generally designated 200. This prosthesis preferably has a slit so as to allow for its easy placement. Thus, once a whole nerve has been repaired in accordance with the procedure set forth for the embodiment of FIG. 10, prosthesis 200 is inserted around the repair site of the injured whole nerve so as to isolate it from the surrounding embodiment. In this regard it is preferable that the ends of prosthesis 200 cover the proximal and distal ends of the severed whole nerve by at least about 3-5 millimeters. Once in place, whole nerve prosthesis 200 provides exceptional stability for the entire nerve repair system.

The present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A nerve prosthesis, comprising:

a tube constructed of biocompatible materials having a first end for enclosing a proximal end of a severed nerve and a second end for enclosing a distal end of the severed nerve, said tube serving to support the severed nerve such that the proximal end of the nerve is positioned in proximity to the distal end of the nerve, said tube being substantially impermeable to fluids associated with the severed nerve;

a coating applied to at least a portion of the interior surface of the tube, said coating comprising a material which substantially adheres to the severed nerve ends within the tube so as to substantially inhibit movement of the severed nerve ends within the tube;

a longitudinal slit formed along the length of the tube, said slit allowing the tube to be longitudinally opened so as to facilitate insertion of the severed nerve ends into the tube;

two longitudinal flaps positioned along the respective edges of the longitudinal slit, said flaps providing for a close seal along the slit when the tube is closed; and means for securing the tube closely around the proximal end of the nerve, wherein the securing means is provided by constructing the wall of the tube of a material having a thickness which provides both resiliency and renitency such that the tube will return to and maintain a longitudinally closed position after having been opened, thereby providing a close seal along the longitudinal slit when the tube is closed.

2. A nerve prosthesis as defined in claim 1 further comprising a coating applied to at least a portion of the exterior surface of the tube and wherein said coating terminates in the longitudinal flaps, said coating comprising a material which does not substantially adhere to body tissue surrounding the severed nerve so as to allow for slippage between the tube and the surrounding body tissue.

3. A nerve prosthesis as defined in claim 2 wherein the tube comprises polyurethane and the exterior coating comprises silicone.

4. A nerve prosthesis as defined in claim 1 wherein the renitent and resilient qualities of the tube are provided by constructing the thickness of the wall of the tube in the range of from about 10% to about 40% of the inner diameter of the tube.

5. A nerve prosthesis as defined in claim 1 wherein the tube is constructed in such a manner as to inhibit retraction of the proximal end of the nerve to not more than 0.5 millimeters from the distal end of the nerve.

6. A nerve prosthesis as defined in claim 5 wherein the tube is configured such that the first end of the tube is long enough to extend over the proximal end of the severed nerve by at least about 3 millimeters.

7. A nerve prosthesis as defined in claim 5 wherein the tube is configured such that the second end of the tube is long enough to extend over the distal end of the severed nerve by at least about 3-4 millimeters.

8. A nerve prosthesis as defined in claim 1 wherein the configuration of the tube is such that it is capable of maintaining the proximal end of the nerve in close proximity with the distal end of the nerve without suturing the nerve ends together.

9. A nerve prosthesis as defined in claim 1 wherein the first and second ends of the tube are slightly tapered.

* * * * *

UNITED STATES PATENT AND TRADEMARK OFFICE
CERTIFICATE OF CORRECTION

PATENT NO. : 4,778,467
DATED : October 18, 1988
INVENTOR(S) : Stensaas et al.

It is certified that error appears in the above-identified patent and that said Letters Patent is hereby corrected as shown below:

Abstract, line 2, "prosthesis" should be --prostheses--
Abstract, line 6, "a epineurial" should be --an epineurial--
Column 2, line 68, "nerve growth factor" should be --nerve growth factors--
Column 4, line 19, "a epinlurial" should be --an epineurial--
Column 5, lines 19-20, "The elongated lamina or endoneurial tube." should be --The elongated Schwann cells are enclosed in an outer, tubular basal lamina or endoneurial tube.--
Column 8, line 49, "it" should be --It--
Column 11, line 2, "referable" should be --preferable--
Column 18, line 59, "substantialy" should be --substantially--
Column 20, line 4, "of of" should be --of--

Signed and Sealed this

Twelfth Day of September, 1989

*Attest:*

DONALD J. QUIGG

*Attesting Officer*    *Commissioner of Patents and Trademarks*